US009643025B2

(12) United States Patent
Crutchfield et al.

(10) Patent No.: US 9,643,025 B2
(45) Date of Patent: *May 9, 2017

(54) MULTI-PRIMARY TRANSFORMER CHARGING CIRCUITS FOR IMPLANTABLE MEDICAL DEVICES

(71) Applicant: Medtronic, Inc., Minneapolis, MN (US)

(72) Inventors: Randolph E Crutchfield, Scottsdale, AZ (US); Mark R Boone, Gilbert, AZ (US); Lonny V Cabelka, San Clemente, CA (US); John T Meador, Half Moon Bay, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,264

(22) Filed: Apr. 24, 2015

(65) Prior Publication Data
US 2016/0067506 A1    Mar. 10, 2016

Related U.S. Application Data

(60) Provisional application No. 62/047,119, filed on Sep. 8, 2014.

(51) Int. Cl.
*A61N 1/39* (2006.01)
*H02J 7/00* (2006.01)
*A61N 1/378* (2006.01)

(52) U.S. Cl.
CPC ......... *A61N 1/3975* (2013.01); *A61N 1/3782* (2013.01); *A61N 1/3956* (2013.01); *H02J 7/007* (2013.01); *H02J 7/0021* (2013.01)

(58) Field of Classification Search
CPC .... A61M 1/125; A61M 1/1031; A61M 1/122; A61M 1/1024; A61M 1/1086;
(Continued)

(56) References Cited

U.S. PATENT DOCUMENTS 2,830,123 A    4/1958 Trousdale
3,222,592 A    12/1965 Kellogg
(Continued)

FOREIGN PATENT DOCUMENTS

EP    0780918 A1    9/1996
EP    0920115 B1    11/2004
(Continued)

OTHER PUBLICATIONS

US 5,674,246, 10/1997, Kroll et al. (withdrawn)
(Continued)

*Primary Examiner* — Rex R Holmes

(57) ABSTRACT

An implantable medical device includes a low-power circuit and a multi-cell power source. The cells of the power source are coupled to a transformer in a parallel configuration. The transformer includes multiple secondary windings and each of the windings is coupled to a capacitor that stores energy for delivery of a therapy to a patient. In accordance with embodiments of this disclosure, the low power circuit is configured to control simultaneous delivery of energy from each of the cells to a plurality of capacitors through the transformer.

23 Claims, 6 Drawing Sheets

(58) Field of Classification Search
CPC ...... A61M 2207/00; A61M 2210/1082; A61M 2210/12; A61B 5/02055; A61F 2/07
See application file for complete search history.

(56) References Cited

U.S. PATENT DOCUMENTS

| | | | |
|---|---|---|---|
| 3,697,808 A | 10/1972 | Lee | |
| 3,770,504 A | 11/1973 | Bergum | |
| 3,824,129 A | 7/1974 | Fagan | |
| 3,888,260 A | 6/1975 | Fischell | |
| 4,119,720 A | 10/1978 | Hardtmann | |
| 4,204,036 A | 5/1980 | Cohen et al. | |
| 4,217,645 A | 8/1980 | Barry et al. | |
| 4,375,817 A | 3/1983 | Engle et al. | |
| 4,595,009 A | 6/1986 | Leinders | |
| 4,800,883 A | 1/1989 | Winstrom | |
| 4,860,185 A | 8/1989 | Brewer | |
| 4,964,877 A | 10/1990 | Keister | |
| 5,137,020 A | 8/1992 | Wayne | |
| 5,147,737 A | 9/1992 | Post et al. | |
| 5,163,427 A | 11/1992 | Keimel | |
| 5,178,140 A | 1/1993 | Ibrahim | |
| 5,188,105 A | 2/1993 | Keimel | |
| 5,221,453 A | 6/1993 | Crespi | |
| 5,235,979 A | 8/1993 | Adams | |
| 5,250,373 A | 10/1993 | Muffoletto et al. | |
| 5,251,624 A | 10/1993 | Bocek et al. | |
| 5,285,779 A | 2/1994 | Cameron | |
| 5,306,581 A | 4/1994 | Taylor | |
| 5,312,458 A | 5/1994 | Muffoletto et al. | |
| 5,360,435 A | 11/1994 | DeGroot | |
| 5,372,605 A | 12/1994 | Adams | |
| 5,383,907 A | 1/1995 | Kroll | |
| 5,434,017 A | 7/1995 | Berkowitz | |
| 5,439,760 A | 8/1995 | Howard | |
| 5,447,522 A | 9/1995 | Chang | |
| 5,458,977 A | 10/1995 | Hosokawa et al. | |
| 5,470,341 A | 11/1995 | Kuehn et al. | |
| 5,543,773 A | 8/1996 | Evans | |
| 5,545,181 A | 8/1996 | Jacobson et al. | |
| 5,549,646 A | 8/1996 | Katz et al. | |
| 5,549,717 A | 8/1996 | Takeuchi et al. | |
| 5,591,212 A | 1/1997 | Keimel | |
| 5,591,218 A | 1/1997 | Jacobson | |
| 5,626,619 A | 5/1997 | Jacobson et al. | |
| 5,656,966 A | 8/1997 | Wilmot et al. | |
| 5,674,248 A | 10/1997 | Kroll | |
| 5,700,280 A | 12/1997 | Silvian | |
| 5,702,431 A | 12/1997 | Wang | |
| 5,814,075 A | 9/1998 | Kroll | |
| 5,825,079 A | 10/1998 | Metzler et al. | |
| 5,836,973 A | 11/1998 | Kroll | |
| 5,994,880 A | 11/1999 | Dropps | |
| 6,008,625 A | 12/1999 | Gan et al. | |
| 6,016,002 A | 1/2000 | Chen | |
| 6,038,473 A | 3/2000 | Olson et al. | |
| 6,040,082 A | 3/2000 | Haas et al. | |
| 6,044,295 A | 3/2000 | Pilz | |
| 6,081,095 A | 6/2000 | Tamura et al. | |
| 6,087,809 A | 7/2000 | Gan | |
| 6,094,597 A * | 7/2000 | Wold | A61N 1/3758 607/5 |
| 6,163,723 A | 12/2000 | Roberts et al. | |
| 6,209,764 B1 | 4/2001 | Hartlaub | |
| 6,238,813 B1 | 5/2001 | Maile et al. | |
| 6,240,318 B1 | 5/2001 | Phillips | |
| 6,269,266 B1 | 7/2001 | Leysieffer | |
| 6,366,817 B1 | 4/2002 | Kung | |
| 6,420,757 B1 | 7/2002 | Metzler | |
| 6,426,628 B1 | 7/2002 | Palm | |
| 6,438,420 B1 | 8/2002 | Thompson | |
| 6,490,484 B2 | 12/2002 | Dooley et al. | |
| 6,549,807 B1 | 4/2003 | Kroll | |
| 6,552,511 B1 | 4/2003 | Fayram | |
| 6,627,337 B2 | 9/2003 | Gan et al. | |
| 6,650,942 B2 | 11/2003 | Howard et al. | |
| 6,671,552 B2 | 12/2003 | Merritt | |
| 6,744,152 B2 | 6/2004 | Kroll | |
| 6,777,908 B2 | 8/2004 | Thorne et al. | |
| 6,909,915 B2 | 6/2005 | Greatbatch | |
| 6,971,391 B1 | 12/2005 | Wang | |
| 7,020,519 B2 | 3/2006 | Greatbatch | |
| 7,079,893 B2 | 7/2006 | Greatbatch | |
| 7,103,404 B2 | 9/2006 | Stadler | |
| 7,120,492 B2 * | 10/2006 | Iverson | H01F 27/2804 607/4 |
| 7,136,701 B2 | 11/2006 | Greatbatch | |
| 7,191,008 B2 | 3/2007 | Schmidt et al. | |
| 7,209,784 B2 | 4/2007 | Schmidt | |
| 7,225,018 B2 | 5/2007 | Iverson et al. | |
| 7,337,001 B2 | 2/2008 | Schmidt | |
| 7,598,706 B2 | 10/2009 | Koski et al. | |
| 7,671,714 B2 | 3/2010 | Tiemeijer | |
| 7,783,357 B2 | 8/2010 | Brink | |
| 7,956,714 B2 | 6/2011 | Ackermann | |
| 7,962,212 B2 | 6/2011 | Signoff | |
| 8,086,312 B2 | 12/2011 | Nielsen | |
| 8,120,262 B2 | 2/2012 | Lee et al. | |
| 8,120,321 B2 | 2/2012 | Vezzini et al. | |
| 8,130,066 B2 | 3/2012 | Dunlap | |
| 8,183,833 B2 | 5/2012 | Kobayashi | |
| 8,209,032 B2 | 6/2012 | Ebert | |
| 8,228,025 B2 | 7/2012 | Ho et al. | |
| 8,447,414 B2 | 5/2013 | Johnson | |
| 8,452,395 B2 | 5/2013 | Crespi | |
| 8,452,399 B2 | 5/2013 | Wanasek | |
| 8,498,716 B2 | 7/2013 | Chen | |
| 8,502,502 B2 | 8/2013 | Huang | |
| 8,508,191 B2 | 8/2013 | Kim et al. | |
| 8,532,785 B1 | 9/2013 | Crutchfield et al. | |
| 8,536,824 B2 | 9/2013 | St-Jacques | |
| 8,588,913 B2 | 11/2013 | Signoff | |
| 8,598,844 B2 | 12/2013 | Densham | |
| 8,612,167 B2 | 12/2013 | Schmidt | |
| 8,649,862 B2 | 2/2014 | Ludwig | |
| 8,901,888 B1 | 12/2014 | Beckman | |
| 8,914,105 B2 | 12/2014 | Wanasek | |
| 8,928,441 B2 | 1/2015 | Prabhakaran | |
| 8,972,005 B2 | 3/2015 | Rasmussen et al. | |
| 2002/0013610 A1 | 1/2002 | Vane et al. | |
| 2003/0042437 A1 | 3/2003 | Worley et al. | |
| 2003/0058659 A1 | 3/2003 | Klinkowstein | |
| 2003/0160588 A1 | 8/2003 | Kroll | |
| 2003/0198866 A1 | 10/2003 | Tanjou et al. | |
| 2004/0044371 A1 | 3/2004 | Tamura et al. | |
| 2004/0147972 A1 | 7/2004 | Greatbatch et al. | |
| 2004/0193227 A1 | 9/2004 | Schmidt | |
| 2004/0267322 A1 | 12/2004 | Kavounas et al. | |
| 2005/0288743 A1 | 12/2005 | Ahn | |
| 2006/0100674 A1 | 5/2006 | Molin | |
| 2006/0111752 A1 | 5/2006 | Greatbatch | |
| 2006/0129192 A1 * | 6/2006 | Greatbatch | A61N 1/375 607/5 |
| 2006/0167496 A1 | 7/2006 | Nelson | |
| 2006/0195148 A1 | 8/2006 | Norton et al. | |
| 2006/0276851 A1 | 12/2006 | Schmidt | |
| 2007/0001796 A1 | 1/2007 | Waffenschmidt et al. | |
| 2007/0150019 A1 | 6/2007 | Youker | |
| 2007/0203528 A1 | 8/2007 | Vernon | |
| 2007/0216368 A1 | 9/2007 | Chandler et al. | |
| 2007/0254212 A1 | 11/2007 | Viavattine | |
| 2008/0015644 A1 | 1/2008 | Julian et al. | |
| 2008/0097544 A1 | 4/2008 | Gahdhi et al. | |
| 2008/0114241 A1 | 5/2008 | Randall et al. | |
| 2008/0223381 A1 | 9/2008 | Schmidt et al. | |
| 2008/0238205 A1 | 10/2008 | Lee | |
| 2009/0157130 A1 | 6/2009 | Ideker et al. | |
| 2009/0157131 A1 | 6/2009 | Ideker et al. | |
| 2009/0322155 A1 | 12/2009 | Oh | |
| 2010/0046251 A1 | 2/2010 | Kyono | |
| 2010/0114248 A1 | 5/2010 | Donofrio et al. | |
| 2011/0003182 A1 | 1/2011 | Zhu | |
| 2011/0127926 A1 | 6/2011 | Samejima et al. | |
| 2011/0149613 A1 | 6/2011 | Lanni | |

(56) References Cited

U.S. PATENT DOCUMENTS

| | | |
|---|---|---|
| 2011/0179637 A1 | 7/2011 | Eberman et al. |
| 2011/0184483 A1 | 7/2011 | Norton |
| 2011/0213434 A1 | 9/2011 | Signoff |
| 2012/0191150 A1 | 7/2012 | Kameli |
| 2012/0265266 A1 | 10/2012 | Colborn |
| 2012/0319495 A1 | 12/2012 | Muller |
| 2013/0088202 A1 | 4/2013 | Kamata et al. |
| 2013/0245718 A1 | 9/2013 | Birkholz et al. |
| 2014/0266102 A1 | 9/2014 | Mikolajczak |
| 2014/0353567 A1 | 12/2014 | Wang et al. |
| 2015/0327963 A1 | 11/2015 | Fregoso et al. |
| 2016/0067506 A1 | 3/2016 | Crutchfield et al. |
| 2016/0067507 A1 | 3/2016 | Cabelka et al. |
| 2016/0067508 A1 | 3/2016 | Boone et al. |
| 2016/0067509 A1 | 3/2016 | Meador et al. |
| 2016/0067510 A1 | 3/2016 | Norton et al. |
| 2016/0067512 A1 | 3/2016 | Norton et al. |
| 2016/0067513 A1 | 3/2016 | Crutchfield et al. |

FOREIGN PATENT DOCUMENTS

| | | |
|---|---|---|
| WO | 94/02202 A1 | 2/1994 |
| WO | 94/22022 A2 | 8/1994 |
| WO | 2006/058028 A2 | 6/2006 |
| WO | 2007/145460 A1 | 12/2007 |

OTHER PUBLICATIONS (PCT/US2015/042328) PCT Notification of Transmittal of the International Search Report and the Written Opinion of the International Searching Authority, Mailed Sep. 30, 2015, 9 pages.

"Design of a Current Controlled Defibrillator" Jonsson, Jorgensen, A Masters Thesis, Department of Industrial Electrical Engineering and Automation, Lund Institute of Technology (Nov. 23, 2004).

"Impedance Matching Transformer Kit, Ideal for Induction Heating and Power Inverters", RMCybernetics, http://www.rmcybernetics.com/shop/matching-transformer (accessed May 16, 2014).

(PCT/US2015/042329) PCT Notification of Transmittal of the International Search Report and the Written Opinion of the International Searching Authority, mailed Jan. 26, 2016, 13 pages.

"Active Cell Balancing in Battery Packs", by Stanislav Arendarik, Freescale Semiconductor, Inc., 2012, 8 pages.

(PCT/US2015/042332) PCT Notification of Transmittal of the International Search Report and the Written Opinion of the International Searching Authority, mailed Oct. 30, 2015, 11 pages.

(PCT/US2015/042331) PCT Notification of Transmittal of the International Search Report and the Written Opinion of the International Searching Authority, mailed Nov. 5, 2015, 11 pages.

Http://www.rmcybernetics.com/shop/matching-transformer, 5 pages, printed Sep. 7, 2016.

Non-Final Office Action for related U.S. Appl. No. 14/695,630 mailed on Apr. 19, 2016 (9 pages).

* cited by examiner

MULTI-PRIMARY TRANSFORMER CHARGING CIRCUITS FOR IMPLANTABLE MEDICAL DEVICES

CROSS-REFERENCE TO RELATED APPLICATIONS

This application claims the benefit of U.S. Provisional Application No. 62/047,119, filed on Sep. 8, 2014. The disclosure of the above application is incorporated herein by reference in its entirety.

The present application is related to commonly-assigned U.S. patent application Ser. No. 14/695,309, which is entitled Implantable Medical Devices Having Multi-Cell Power Sources; U.S. patent application Ser. No. 14/695,447, which is entitled Multiple Transformer Charging Circuits for Implantable Medical Devices; U.S. patent application Ser. No. 14/695,630, which is entitled Transformer-Based Charging Circuits for Implantable Medical Devices; U.S. patent application Ser. No. 14/695,948, which is entitled Implantable Medical Devices Having Multi-Cell Power Sources; U.S. patent application Ser. No. 14/695,887, which is entitled Transthoracic Protection Circuit for Implantable Medical Devices; and U.S. patent application Ser. No. 14/695,826, which is entitled Monitoring Multi-Cell Power Source of an Implantable Medical Device, all of which are filed concurrently herewith and all of which are incorporated herein by reference in their entireties.

FIELD

The present disclosure relates to body implantable medical devices and, more particularly to circuits and techniques implemented in an implantable medical device to provide an electrical therapeutic output.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with implantable medical devices.

Implantable medical electrical leads are used with a wide variety of these implantable medical devices. The medical leads may be configured to allow electrodes to be positioned at desired cardiac locations so that the device can monitor and/or deliver stimulation therapy to the desired locations. For example, electrodes on implantable leads may detect electrical signals within a patient, such as an electrocardiogram, in addition to delivering electrical stimulation.

Currently, ICD's use endocardial or epicardial leads which extend from the ICD housing through the venous system to the heart. Electrodes positioned in or adjacent to the heart by the leads are used for pacing and sensing functions. Cardioversion and defibrillation shocks are generally applied between a coil electrode carried by one of the leads and the ICD housing, which acts as an active can electrode.

A subcutaneous implantable cardioverter defibrillator (SubQ ICD) differs from the more commonly used ICD's in that the housing and leads are typically implanted subcutaneously such that the sensing and therapy are accomplished subcutaneously. The SubQ ICD does not require leads to be placed in the heart or in contact with the heart. Instead, the SubQ ICD makes use of one or more electrodes on the housing, together with a subcutaneous lead that carries a defibrillation coil electrode and a sensing electrode.

The implantable medical devices are typically battery powered and often utilize capacitors or other electrical charge storage components to hold an electrical output to be made available to a patient. Due to the nature of defibrillation therapy or other high voltage therapy, it is not practical for the implantable medical device to supply the energy upon instantaneous demand by drawing from the power source. Instead, additional circuitry is provided to transfer and store the energy from the power source to accumulate a desired voltage level.

However, the placement of the SubQ ICD lead(s) and electrode(s) outside the heart presents a challenge to generating sufficient energy levels that are required to deliver appropriate therapy. As described herein, the present disclosure addresses the need in art to provide circuitry and techniques for generating appropriate electrical stimulation therapy in a SubQ ICD system.

SUMMARY

In accordance with aspects of this disclosure, circuits and techniques implemented in an implantable medical device are provided for generating an electrical stimulation therapy from a multi-cell power source. Such electrical stimulation therapy exhibits an output having a higher voltage than the voltage available directly from the battery or a higher current than the current available directly from the battery.

In accordance with embodiments of the present disclosure, implantable medical devices may include one or more of the following features: (a) a transformer having a magnetic core, a plurality of primary windings wound around the core, and a plurality of secondary windings wound around the core and magnetically coupled to the plurality of primary windings, (b) a power source having at least a first cell and a second cell, the first and second cells being coupled to the plurality of primary windings in a parallel configuration, (c) a plurality of capacitors coupled in a series configuration, wherein each of the plurality of capacitors is coupled to a single winding of the plurality of secondary windings, (d) and a low power circuit coupled to the power source for controlling the delivery of charge from the power source to the plurality of capacitors through the transformer.

In further aspects of the embodiments of the present disclosure, the low power circuit of the implantable medical devices is configured to control simultaneous delivery of energy from each of the first and second cells to the plurality of capacitors through the transformer.

In further aspects of the embodiments of the present disclosure, the implantable medical devices further comprise a first switching element configured to selectively couple the first cell to the plurality of primary windings and a second switching element configured to selectively couple the second cell to the plurality of primary windings.

In further aspects of the embodiments of the present disclosure, the implantable medical device further comprise a monitoring circuit for monitoring a state of charge of each of the first and second cells.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

Figure 1:
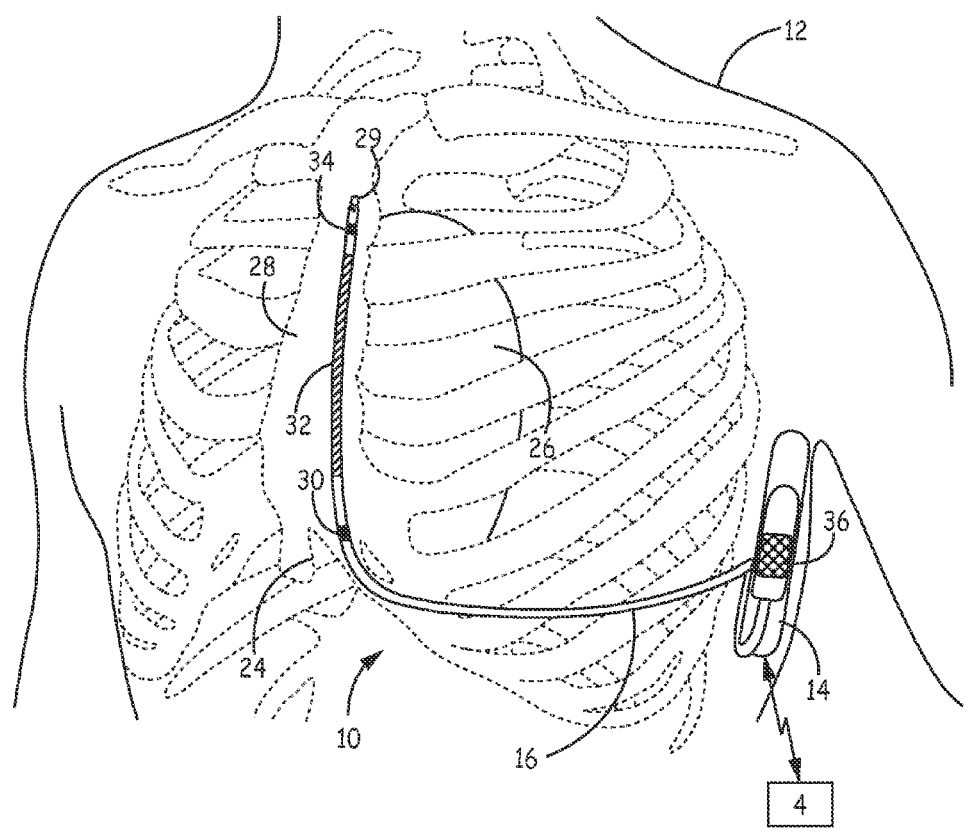
FIG. 1 is a front view of a patient implanted with an implantable cardiac system.
Figure 2:
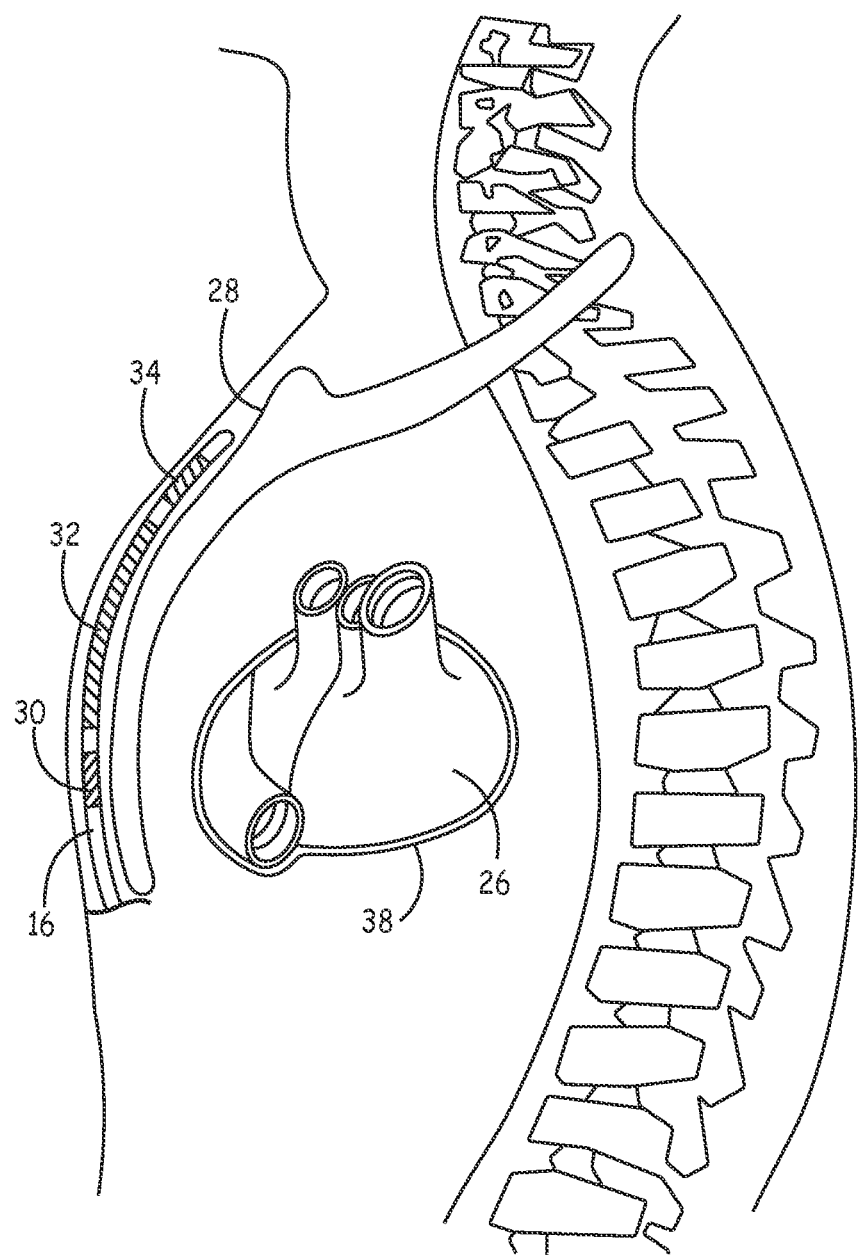
FIG. 2 is a side view the patient implanted with an implantable cardiac system.
Figure 3:
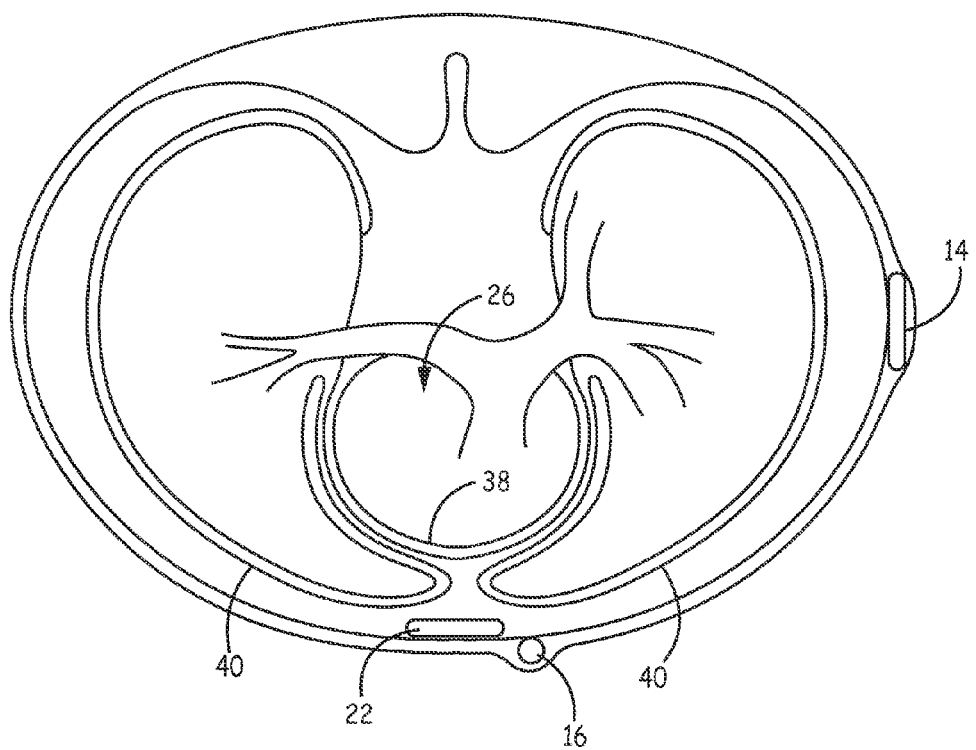
FIG. 3 is a transverse view of the patient implanted with an implantable cardiac system.

FIGS. 1-3 are conceptual diagram of a patient 12 implanted with an example extravascular cardiac defibrillation system 10. In the example illustrated in FIG. 1, extravascular cardiac defibrillation system 10 is an implanted subcutaneous defibrillation system for purposes of illustration.

Extravascular cardiac defibrillation system 10 includes an implantable medical device such as implantable cardiac defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24 defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

ICD 14 may interact with an external device 4 such as a patient programmer or a clinician programmer via a 2-way telemetry link. Such a programmer communicates with ICD 14 via telemetry as is known in the art. The programmer 4 may thereby establish a telemetry session with ICD 14 to provide programs, instructions, parameters, data, and other information to ICD 14, and to likewise receive status, data, parameters, programs, and other information from the ICD 14. Status information received from the ICD 14 may include data about the remaining longevity of the power source (e.g., a battery) based on the amount of charge that has thus far been delivered by the battery and consumed by the ICD 14 as compared to when the battery was in the full-charged state ("battery capacity"). Status information may also include an "Elective Replacement Indicator" (ERI) to indicate when surgery must be scheduled to replace ICD 14. Status may also include an "End of Life" (EOL), which is activated to signify end-of-battery life.

Defibrillation lead 16 is placed along sternum 28 such that a therapy vector between defibrillation electrode 32 and a second electrode (such as a housing or can electrode 36 36 of ICD 14 or an electrode placed on a second lead) is substantially across the ventricle of heart 26. The therapy vector may, in one example, be viewed as a line that extends from a point on the defibrillation electrode 32 to a point on the housing or can electrode 36 of ICD 14. In another example, defibrillation lead 16 may be placed along sternum 28 such that a therapy vector between defibrillation electrode 32 and a housing or can electrode 36 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 32, 34, and 30, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing that forms a hermetic seal that protects components within ICD 14. The housing of ICD 14 may be formed of a conductive material, such as titanium or other biocompatible conductive material or a combination of conductive and non-conductive materials. In some instances, the housing of ICD 14 functions as an electrode (sometimes referred to as a housing electrode or can electrode) that is used in combination with one of electrodes 32, 34, or 30 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. The housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 32, 34, and 30. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 32, 34 and 30, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 32, 34 and 30. In other words, each of the one or more elongated electrical conductors contained within the lead body of defibrillation lead 16 may engage with respective ones of electrodes 32, 34 and 30. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 32, 34 and 30 and transmit sensed electrical signals from one or more of electrodes 32, 34 and 30 to the sensing module within ICD 14.

ICD 14 may sense electrical activity of heart 26 via one or more sensing vectors that include combinations of electrodes 34 and 30 and a housing or can electrode 36 of ICD 14. For example, ICD 14 may obtain electrical signals sensed using a sensing vector between electrodes 34 and 30, obtain electrical signals sensed using a sensing vector between electrode 34 and the conductive housing or can electrode 36 of ICD 14, obtain electrical signals sensed using a sensing vector between electrode 30 and the conductive housing or can electrode 36 of ICD 14, or a combination thereof. In some instances, ICD 14 may even sense cardiac electrical signals using a sensing vector that includes defibrillation electrode 32, such as a sensing vector between defibrillation electrode 32 and one of electrodes 34 or 30, or a sensing vector between defibrillation electrode 32 and the housing or can electrode 36 of ICD 14.

ICD 14 may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 32 of defibrillation lead 16 and the housing/can electrode. Defibrillation electrode 32 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 34 and 30 and/or the housing/can electrode. Electrodes 34 and 30 may comprise ring electrodes, hemispherical electrodes, coil electrodes, helix electrodes, segmented electrodes, directional electrodes, or other types of electrodes, or combination thereof. Electrodes 34 and 30 may be the same type of electrodes or different types of electrodes, although in the example of FIG. 1 both electrodes 34 and 30 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29. In this case, defibrillation lead 16 may be connected to or secured to an implant tool via an interference fit as will be described in more detail herein. An interference fit, sometimes also referred to as a friction fit, is a fastening between two parts which is achieved by friction after the parts are pushed together, rather than by any other means of fastening.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 30 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs and/or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the implant tools described herein may be utilized to implant the lead at a pericardial or epicardial location outside the heart 26. Moreover, implant tools such as those described herein may be used to implant non-cardiac leads in other locations within patient 12.

In an example, lead 16 may be placed in the mediastinum and, more particularly, in the anterior mediastinum. The anterior mediastinum is bounded laterally by pleurae 40, posteriorly by pericardium 38, and anteriorly by sternum 22. Lead 16 may be implanted within the mediastinum such that one or more electrodes 32 and 34 are located over a cardiac silhouette of the ventricle as observed via fluoroscopy. In the example illustrated in FIGS. 1-3, lead 16 is located substantially centered under sternum 22. In other instances, however, lead 16 may be implanted such that it is offset laterally from the center of sternum 22. Although described herein as being implanted in the substernal space, the mediastinum, or the anterior mediastinum, lead 16 may be implanted in other extra-pericardial locations.

Electrodes 30, 32, and 34 may comprise ring electrodes, hemispherical electrodes, coil electrodes, helical electrodes, ribbon electrodes, or other types of electrodes, or combinations thereof. Electrodes 30, 32 and 34 may be the same type of electrodes or different types of electrodes. In the example illustrated in FIGS. 1-3 electrode 34 is a coil electrode and electrodes 30 and 34 are ring, or hemispherical electrodes.

Figure 4:
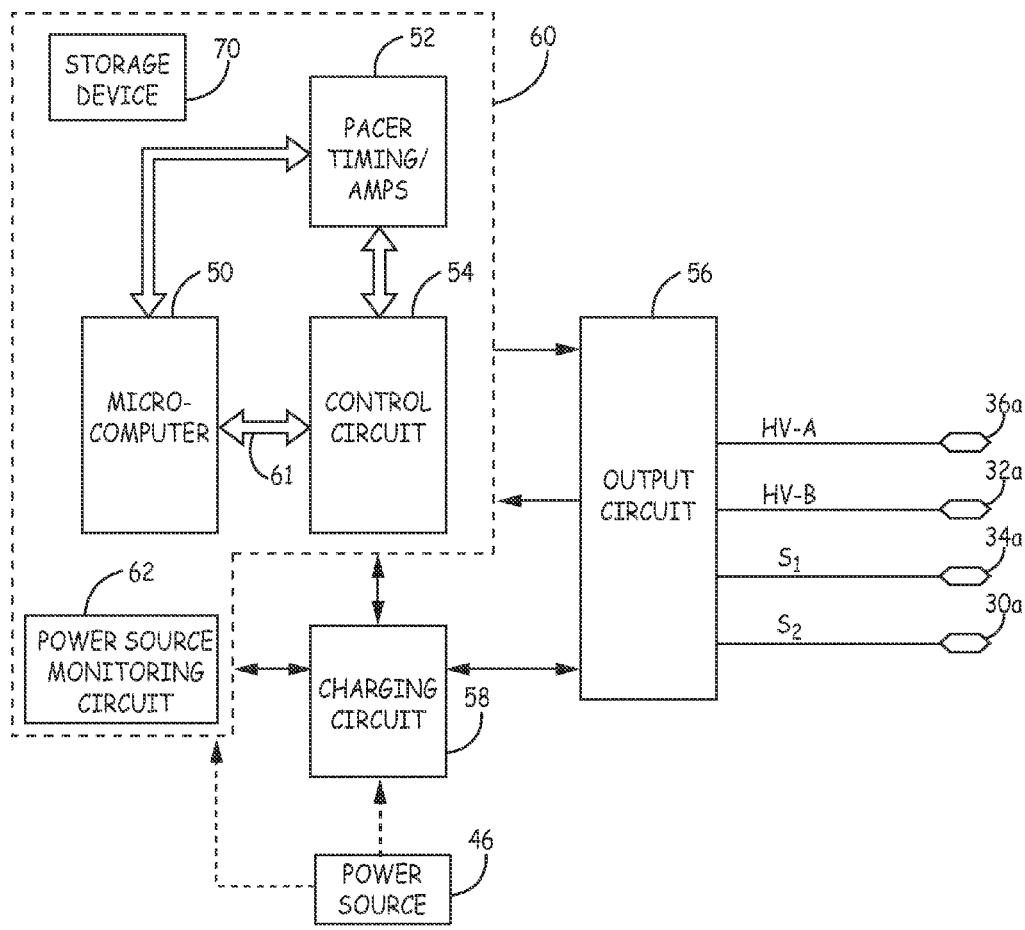
FIG. 4 depicts a schematic diagram of an embodiment of operational circuitry included in an implantable cardiac defibrillator of the cardiac system of FIGS. 1-3.

FIG. 4 is a schematic diagram of operational circuitry 48 included in ICD 14 according to an embodiment of the present disclosure. It is understood that the system of FIG. 4 includes both low power circuitry and high power circuitry. The present disclosure may be employed in a device that provides either or both of a high power electrical stimulation therapy, such as a high power defibrillation therapy, or a low power electrical stimulation therapy, such a pacing pulse, or both. Accordingly, the components in the operational circuitry 48 may support generation and delivery of either one or both such therapies. For ease of description, this disclosure will describe an operational circuitry 48 that supports only a high power electrical stimulation therapy, such as cardioversion and/or defibrillation stimulation therapy. However, it should be noted that the operational circuitry 48 may also provide defibrillation threshold (DFT) induction therapy or post-shock pacing such as anti-tachycardia pacing (ATP) therapy.

The operational circuitry 48 is provided with at least one or more power sources 46 which may include a rechargeable and/or non-rechargeable battery having one or more cells. As used in this disclosure, the term "cell" refers to a battery cell which, as is understood in the art, includes an anode terminal and a cathode terminal. An example of a battery cell is set forth in commonly assigned U.S. Patent Application No. US 2011/0179637 "Implantable Medical Devices with Low Volume Batteries, and Systems", to Norton which is incorporated herein by reference. As described in greater detail below, the power source 46 can assume a wide variety of forms. Similarly, the operational circuitry 48, which includes the low power circuit 60 and the output circuit 56, can include analog and/or digital circuits, can assume a variety of configurations, and is electrically connected to the power source 46.

A power source monitoring circuit 62 is provided for monitoring the magnitude of residual energy and/or rate of depletion of energy from the power source 46. The monitoring circuit 62 may monitor the power source by measuring a parameter that is, for example, indicative of the residual energy or rate of discharge, of the power source 46. The monitoring circuit 62 may employ techniques that involve computing the indication of the residual energy, or rate of discharge, of the power source 46 (or individual cells) utilizing a parameter such as the voltage across terminals of power source 46. In other embodiments, monitoring circuit 62 may alternatively or additionally have the capability to measure a parameter such as current flowing from the power source 46. Any known battery monitoring techniques, such as coulomb counting or a direct voltage measurement may be utilized to monitor the state of charge of the individual cells.

The output circuit 56 and the low power circuit 60 are typically provided as part of an electronics module associated with the ICD 14. In general terms, the output circuit 56 is configured to deliver an electrical pulse therapy, such as a defibrillation or a cardioversion/defibrillation pulse. In sum, the output circuit 56 is responsible for applying stimulating pulse energy between the various electrodes 28-34 (FIG. 1) of the ICD 14. As is known in the art, the output circuit 56 may be associated with a capacitor bank (not shown) for generating an appropriate output energy, for example in the range of 0.1-40 Joules.

The low power circuit 60 is similarly well known in the art. In general terms, the low power circuit 60 monitors heart activity and signals activation of the output circuit 56 for delivery of an appropriate stimulation therapy. Further, as known in the art, the low power circuit 60 may generate a predetermined series of pulses from the output circuit 56 as part of an overall therapy.

In an embodiment, ICD 14 functions are controlled by means of stored software, firmware and hardware that cooperatively monitor the EGM, determine when a cardioversion or defibrillation shock necessary, and deliver prescribed defibrillation therapies. The schematic diagram of FIG. 4 incorporates circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, for example, both incorporated herein by reference in their entireties, for selectively delivering single phase, simultaneous biphasic and sequential biphasic cardioversion-defibrillation stimulation therapy. In an exemplary implementation, IMD 14 may deliver stimulation therapy employing housing electrode 36 coupled to the terminal HV-A and at least one electrode such as electrode 32 coupled to the node HV-B output (at terminals 36a and 32a, respectively) of the output circuit 56. In alternative embodiments, the IMD 14 may employ additional electrodes such as electrodes 30, 34 coupled to nodes such as S1, S2 (at terminals 30a and 34a, respectively) for sensing or stimulation therapy.

The cardioversion-defibrillation stimulation therapy energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICD 14 using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The SubQ ICD 14 of the present disclosure uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation stimulation therapies are only delivered when a malignant tachyarrhythmia, e.g., ventricular fibrillation is detected through processing of the far field cardiac ECG employing one of the available detection algorithms known in the ICD 14 art.

In FIG. 4, pacer timing/sense amplifier circuit 52 processes the far field ECG SENSE signal that is developed across a particular ECG sense vector defined by a selected pair of the electrodes 36, 32, and optionally, electrodes 30, 34 if present as noted above. The selection of the sensing electrode pair is made through a control circuit 54 in a manner to provide the most reliable sensing of the EGM signal of interest, which would be the R wave for patients who are believed to be at risk of ventricular fibrillation leading to sudden death. The far field ECG signals are passed through the control circuit 54 to the input of a sense amplifier in the pacer timing/sense amplifier circuit 52.

Control circuit 54 may comprise one or more microprocessors, Application-Specific Integrated Circuits (ASICs), Digital Signal Processors (DSPs), Field-Programmable Gate Arrays (FPGAs), discrete electronic components, state machines, sensors, and/or other circuitry. Control circuit 54 may operate under the control of programmed instructions such as software and/or firmware instructions stored within a storage device (70). The storage device may include volatile, non-volatile, magnetic, optical, and/or electrical media for storing digital data and programmed instructions, including Random Access Memory (RAM), Read-Only Memory (ROM), Non-Volatile RAM (NVRAM), Electrically Erasable Programmable ROM (EEPROM), flash memory, removable storage devices, and the like. These one or more storage devices 70 may store programs executed by control circuit 54.

Storage devices 70 may likewise store data, which may include, but is not limited to, programmed parameters, patient information, data sensed from the patient, and status information indicating the status of the ICD 14. For instance, the data may include statistical information and other characteristic data about the battery (or individual cell) that is used to predict charge remaining within the power source 46 of ICD 14 as will be discussed in more detail below. The data may further contain ERI and/or EOL indicators to indicate when replacement operations will be needed. This information may be provided to a clinician or patient via the external device 4.

Detection of a malignant tachyarrhythmia is determined via the control circuit 54 as a function of one or more sensed signals (e.g., R-wave signals and/or P-wave signals) that are output from the pacer timing/sense amplifier circuit 52 to the control circuit 54. An example detection algorithm is described in U.S. Pat. No. 7,103,404, titled "Detection of Tachyarrhythmia Termination", issued to Stadler, which is incorporated herein by reference in its entirety. Certain steps in the performance of the detection algorithm criteria are cooperatively performed in a microcomputer 50, including stored detection criteria that may be programmed into via a telemetry interface (not shown) conventional in the art.

The microcomputer 50 is generally representative of a processor and associated memory in storage device 70. The memory may reside internally within the microcomputer 50, or separately in storage device 53. The memory, for example, may include computer readable instructions that, when executed by processor, cause the operational circuitry and or any other component of the medical device to perform various functions attributed to them. For example, the memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Such memory will typically be non-transitory. The processor, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions attributed to the microcomputer 50 may be embodied as software, firmware, hardware, or any combination thereof.

Data and commands are exchanged between microcomputer 50 and control circuit 54, pacer timing/amplifier circuit 52, and output circuit 56 via a bi-directional data/control bus 61. The pacer timing/amplifier circuit 52 and the control circuit 54 are clocked at a slow clock rate. The microcomputer 50 is normally asleep, but is awakened and operated by a fast clock by interrupts developed by sensed cardiac events or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 52.

The detection algorithms are highly sensitive and specific for the presence or absence of life threatening ventricular arrhythmias, e.g., ventricular tachycardia (V-TACH) and ventricular fibrillation (V-FIB). As discussed above, the detection algorithms contemplated in accordance with this disclosure may utilize sensed cardiac signals to detect the arrhythmias. In addition, detection algorithms for atrial fibrillation may also be included.

Although the ICD 14 of the present disclosure may rarely be used for an actual sudden death event, the simplicity of design and implementation allows it to be employed in large populations of patients at modest risk with modest cost by medical personnel other than electrophysiologists. Consequently, the ICD 14 of the present disclosure includes the automatic detection and therapy of the most malignant rhythm disorders.

When a malignant tachycardia is detected, high voltage capacitors (not shown) within the output circuit are charged to a pre-programmed voltage level by a charging circuit 58. It is generally considered inefficient to maintain a constant charge at all times on the high voltage capacitors. Instead, charging is initiated when control circuit 54 issues a high voltage charge command delivered to charging circuit 58 and charging is controlled by means of bi-directional signal line(s) from the HV output circuit 56. Without intending to be limiting, the high voltage output capacitors may comprise film, aluminum electrolytic or wet tantalum construction. Some examples of the high voltage output capacitors are described in commonly assigned U.S. Pat. No. 8,086,312, titled "Capacitors for Medical Devices", issued to Nielsen, which is incorporated herein by reference in its entirety.

The high voltage output capacitors may be charged to very high voltages, e.g., 700-3150V, to be discharged through the body and heart between the selected electrode pairs among first, second, and, optionally, third and/or fourth subcutaneous cardioversion-defibrillation electrodes 36, 32, 30, 32. The details of an exemplary charging circuit 58 and output circuit 56 will be discussed below. The high voltage capacitors are charged by charging circuit 58 and a high frequency, high-voltage transformer. The state of capacitor charge is monitored by circuitry within the output circuit 56 that provides a feedback signal indicative of the voltage to the control circuit 54. Control circuit 54 terminates the high voltage charge command when the received signal matches the programmed capacitor output voltage, i.e., the cardioversion-defibrillation peak shock voltage.

Control circuit 54 then develops a control signal that is applied to the output circuit 56 for triggering the delivery of cardioverting or defibrillating shocks. In this way, control circuitry 54 serves to control operation of the high voltage output stage 56, which delivers high energy cardioversion-defibrillation stimulation therapies between a selected pair or pairs of the first, second, and, optionally, the third and/or fourth cardioversion-defibrillation electrodes 36, 32, coupled to the HV-A, HV-B and optionally electrodes 34, 30 coupled to the S1, S2 terminals as shown in FIG. 4.

Thus, ICD 14 monitors the patient's cardiac status and initiates the delivery of a cardioversion-defibrillation stimulation therapy through a selected pair or pairs of the first, second, third and/or fourth electrodes 36, 32, 34, and 30 in response to detection of a tachyarrhythmia requiring cardioversion-defibrillation.

Typically, the charging cycle of the capacitors has a short duration, e.g., it can take anywhere from two seconds to about thirty seconds, and occurs very infrequently. The ICD 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation stimulation therapy can be stored in RAM for uplink telemetry transmission to an external programmer as is well known in the art to facilitate in diagnosis of the patient's cardiac state.

Housing 14 may include a telemetry circuit (not shown in FIG. 4), so that it is capable of being programmed by means of external device 4 (FIG. 1) via a 2-way telemetry link. Uplink telemetry allows device status and diagnostic/event data to be sent to external programmer for review by the patient's physician. Downlink telemetry allows the external programmer via physician control to allow the programming of device function and the optimization of the detection and therapy for a specific patient. Programmers and telemetry systems suitable for use in the practice of the present disclosure have been well known for many years. Known programmers typically communicate with an implanted device via a bi-directional telemetry link such as Bluetooth®, radio-frequency, near field, or low frequency telemetry link, so that the programmer can transmit control commands and operational parameter values to be received by the implanted device, and so that the implanted device can communicate diagnostic and operational data to the programmer.

Those skilled in the art will appreciate that the various components of the low power circuit 60 i.e., pacer/sense circuit 52, control circuit 54, and microcomputer 50 are illustrated as separate components for ease of discussion. In alternative implementations, the functions attributed to these components 50, 52 and 54 may suitably be performed by a sole component.

As mentioned above, the control circuit 54 and output circuit 56 performs several functions. One of those is to monitor the state of capacitor charge of the high voltage output capacitors. Another function is to allow the controlled transfer of energy from the high voltage output capacitors to the patient.

Figure 5:
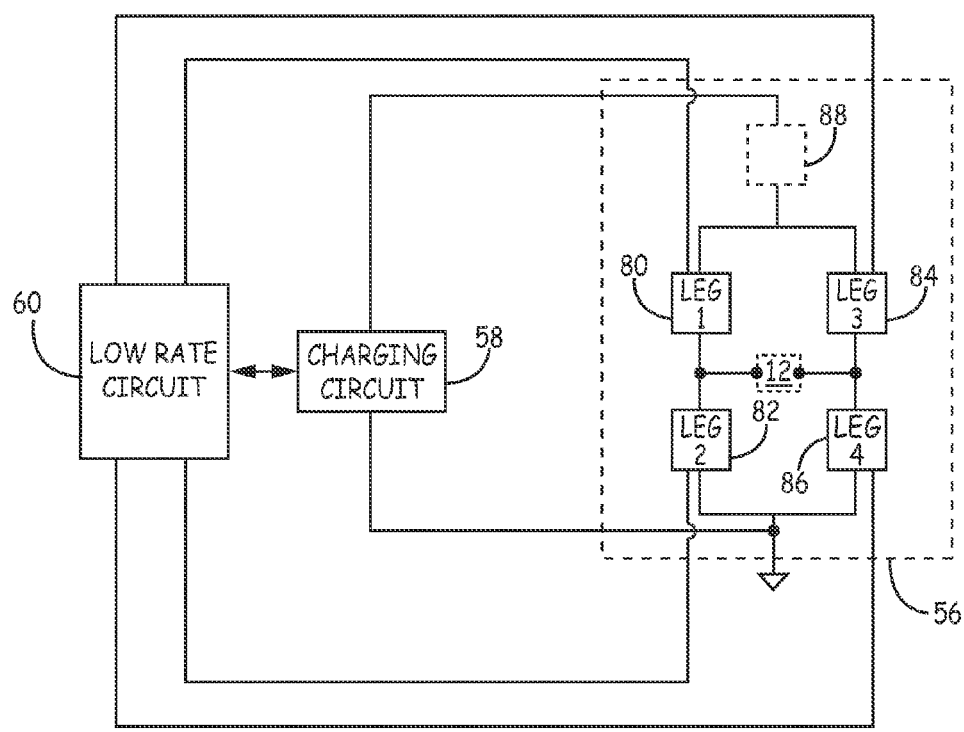
FIG. 5 illustrates an exemplary schematic diagram showing a portion of the operational circuitry of FIG. 4 in accordance with an embodiment of the disclosure.

FIG. 5 illustrates an exemplary schematic showing a portion of the operational circuitry 48 of FIG. 4, in accordance with an embodiment of the disclosure, in greater detail. The output circuit 56 allows the controlled transfer of energy from the energy storage capacitors to the patient 12.

The output circuit 56 includes four legs 80, 82, 84, and 86 that are interconnected. The interconnection of the four legs with legs 80 and 82 being configured in a parallel orientation alongside legs 84 and 86 and a bridge being provided to intersect each of the pair of parallel connected legs. As is shown in FIG. 5, the interconnected legs are arrayed to define a configuration includes a high side and a low side that may resemble a "H". In other words, the four interconnected legs are arrayed having legs 80 and 84 defining the high side and legs 82 and 86 defining the low side.

The intersecting bridge includes HV-A and HV-B terminals that couple the output circuit 56 to the cardioversion electrodes 36 and 32. As previously described, patient 12 is connectable (e.g., using leads/electrodes 36, 32 and any other suitable connections) between terminal HV-A located between the switch 80 and switch 82 and terminal HV-B located between switch 84 and switch 86.

Legs 80 and 84 are coupled to a positive terminal of the energy storage capacitors. An optional discharge switch 88, such as an insulated gate bipolar transistor (IGBT), may be used in the coupling from the legs 80 and 84 to the positive terminal of the energy storage capacitors. Discharge switch 88 may be controlled by control circuit 54 (FIG. 4) that is included within the low power circuit 60 to close and remain in the conducting state during discharge of the capacitors. Leg 82 and 86 are coupled to a negative terminal of the energy storage capacitors. The selection of one or more of the switches 80, 82, 84, 86 under control of control circuit 54 may be used to provide one or more functions. For example, selection of certain switches in one or more configurations may be used to provide one or more types of stimulation pulses, or may be used to provide active or passive recharge, etc.

For example, in accordance with an embodiment, the ICD 14 provides a biphasic defibrillation pulse to the patient in the following manner. With reference to FIG. 5, once the energy storage capacitors are charged to a selected energy level, the switches 80, 86, and 88 are closed so as to provide a path from the capacitors to electrode 36, 32 for the application of a first phase of a defibrillation pulse to the patient 12. The stored energy travels from the positive terminal of the capacitors, through switch 88 through switch 80, across the patient 12, back through switch 86 to the negative terminal of the capacitors. The first phase of the biphasic pulse therefore applies a positive pulse from the electrode 36 to the electrode 32.

After the end of the first phase of the biphasic defibrillation pulse, the switches 88, 84 and 82 are switched on to start the second phase of the biphasic pulse. Switches 84 and 82 provide a path to apply a negative defibrillation pulse to the patient 12. With reference to FIG. 5, the energy travels from the positive terminal of the capacitors, through switch 88 to switch 84, across the electrodes 32, 36 coupled to the patient 12, and out through switch 82 to the negative terminal of the capacitors. The polarity of the second phase of the defibrillation pulse is therefore opposite in polarity to the first phase of the pulse.

Figure 6:
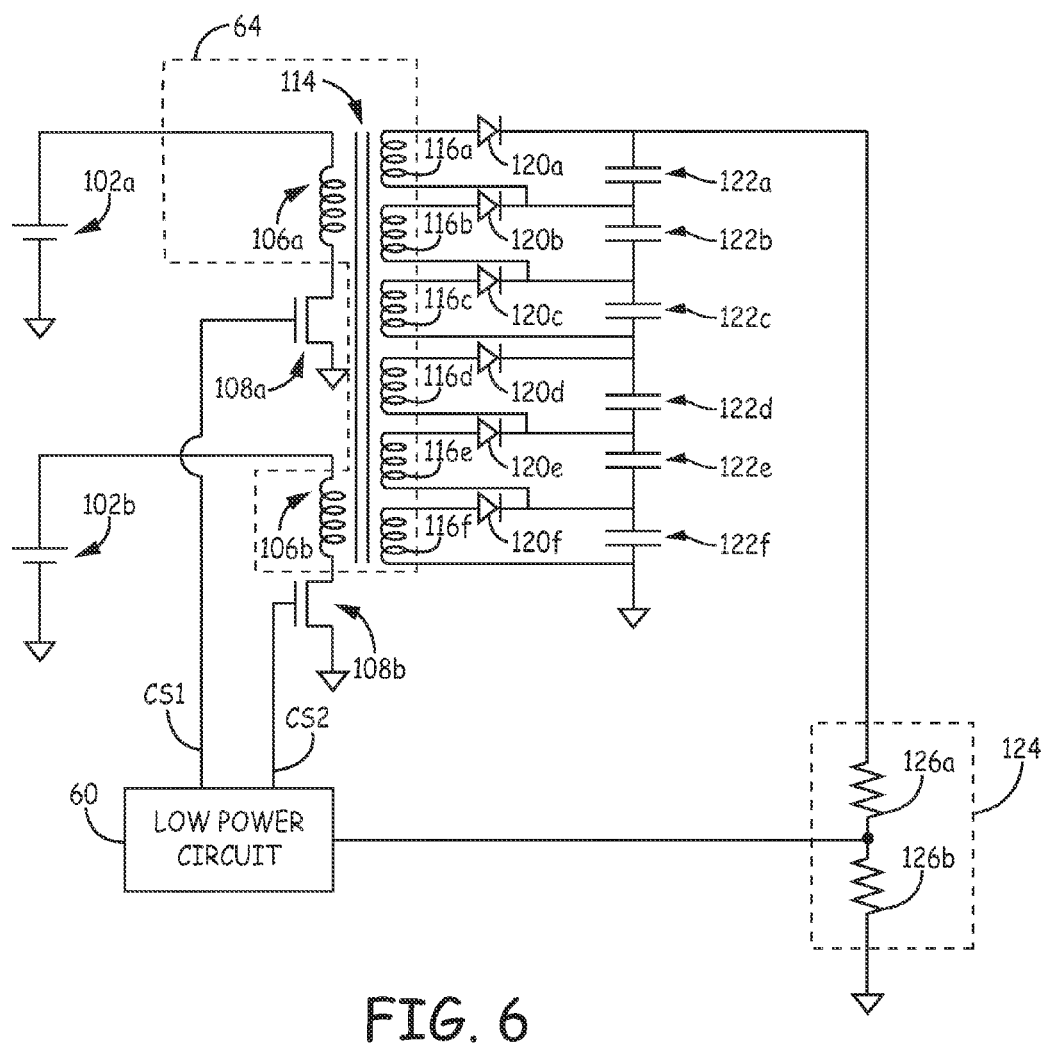
FIG. 6 illustrates an exemplary schematic diagram showing a portion of the operational circuitry of FIG. 4 in accordance with an embodiment of the disclosure.

FIG. 6 is a schematic illustrating a portion of the operational circuit 48 of IMD 14. As previously mentioned, the operational circuit 48 includes at least one power source 46. The power source 46 may comprise a battery having at least two cells 102a, 102b (collectively "102"). In exemplary embodiments, the power source 46 may be programmable or static and may be a switched or linear regulated source, etc.

In an embodiment, the cells 102 supply power to the operational circuit 48 as well as the charge for stimulation therapy energy. The cells 102 may be formed from materials such as LiCFx, LiMnO2, LiI2, LiSVO or LiMnO2, among others, as is known in the art.

Each of the cells 102 is coupled to a transformer 64 that is included within the output circuit 56 (shown in dashed lines in FIG. 6). In an embodiment, the transformer 64 may be configured as a dual primary transformer having a first primary winding 106a and a second primary winding 106b. In the embodiment, the cell 102a is coupled to the first primary winding 106a and the cell 102b is coupled to the second primary winding 106b. In the embodiment, two primary windings 106a-b are shown although it is to be understood that, in alternative embodiments, additional primary windings may be included that would couple to a power supply having greater than two cells. For example, in one example embodiment, a power source that includes three cells would correspondingly include three primary windings.

The transformer 64 further includes a common core 114 and a plurality of secondary windings 116a-f. In the embodiment, six second windings 116a-f are shown although it is to be understood that, in alternative embodiments, the plurality of secondary windings may comprise any other integer number of windings greater than two (2). Both primary windings 106a, 106b are wound around the common core 114 and the plurality of secondary windings 116a-f are also wound around the common core 114. As such, all the secondary windings 116a-f share the magnetic flux and output an identical voltage.

A first switch 108a is coupled between the first primary winding 106a of the transformer and the cell 102a. A second switch 108b is coupled between the second primary winding 106b of the transformer 64 and the cell 102a. Each of the switches 108a, 108b is coupled to a charge monitoring circuit, such as control circuit 54 (FIG. 4), which issues control signals (CS1, CS2) to selectively actuate each of the switches 108a, 108b. The control signals may be issued to selectively actuate the switches 108a, 108b separately, simultaneously, or in any other desired manner. For example, the control signal may be issued as a function of the residual energy of each of the cells 102. In one example, it may be desired that the voltage difference between the first and second cells 102 should be within a predetermined criteria, such as within a selected range, or no greater than a predetermined voltage value. As such, the total energy in each of the first and second cells 102 may be measured and evaluated to determine whether the predetermined criterion is met. If the criterion is met e.g., difference is within the predetermined range of voltage values, the control signals may be issued to simultaneously couple both cells 102 so as to draw energy from both cells 102 simultaneously. However, if the criterion is not met, e.g., difference exceeds the predetermined voltage value, the control signals may be timed to couple the cells 102 at different times so as to draw energy from the cell 102 having the higher magnitude of energy first until the criterion for the voltage difference is met.

The cells 102 may be formed such that each cell includes a cathode (positive) terminal and an anode (negative) terminal. As is illustrated in the depicted embodiment, the cathode terminals of cells 102a, 102b are coupled to the primary winding 106a and the primary winding 106b, respectively, and the anode terminals are both connected to a common node, such as the circuit ground node. The switches 108a, 108b are also coupled to the common node.

As such, a first circuit path is defined between the first cell 102a and first primary winding 106a and a second circuit path is defined between the second cell 102b and the primary winding 106b. In an alternative embodiment, the anode terminals of the cells 102a, 102b are coupled to the primary winding 106a and the primary winding 106b, respectively, and each of the cathode terminals is connected to a common node, such as the circuit ground node.

In one embodiment, the switches 108 are simultaneously actuated to a conducting state to enable current to flow from both cells 102 to the transformer 64. The actuation of the first switch 108a into a closed position initiates current flow from the first cell 102a to the first primary winding 106a and actuation of the second switch 108b into a closed position initiates current flow from the second cell 102b to the second primary winding 106b. In other words, the closing of switch 108a creates a current path for flow of current from the first cell 102a to the first primary winding 106a while the closing of switch 108b creates a current path for flow of current from the second cell 102b to the second primary winding 106b.

Each of the secondary windings 116a-f is coupled to a capacitor for storage of the charge generated by the transformer 64. Specifically, secondary winding 116a is coupled to capacitor 122a, secondary winding 116b is coupled to capacitor 122b, secondary winding 116c is coupled to capacitor 122c, secondary winding 116d is coupled to capacitor 122d, secondary winding 116e is coupled to capacitor 122e, and secondary winding 116f is coupled to capacitor 122f. The capacitors 122a-f are all coupled in series.

A diode may optionally be coupled between each of the secondary windings and the respectively coupled capacitor to bias the flow of current from the transformer to each of the capacitors. Specifically, a diode 120a is coupled between secondary winding 116a and capacitor 122a, a diode 120b is coupled between secondary winding 116b and capacitor 122b, a diode 120c is coupled between secondary winding 116c and capacitor 122c, a diode 120d is coupled between secondary winding 116d and capacitor 122d, a diode 120e is coupled between secondary winding 116e and capacitor 122e, and a diode 120f is coupled between secondary winding 116f and capacitor 122f. In the embodiment of FIG. 6, the diodes are illustrated for completeness but it should be understood that in alternate embodiments, the diodes 120a-f need not be included.

As shown in FIG. 6, the cells 102 are arranged in a parallel configuration and each cell 102a, 102b simultaneously delivers charge to its respective primary winding 106a, 106b.

Although not shown in the figure, an isolation circuit may be provided to enable coupling of the cells 102 to other circuitry of IMD 14. Such an isolation circuit enables the cells 102 to deliver current during high power current operations while allowing both cells to contribute to the current supply to other circuitry such as circuits 50, 52, and/or 54 of operational circuit 48 (shown in FIG. 4) during low power current operations. The high power current operations include the delivery of energy to the transformer 64 to, for example, provide defibrillation therapy and other electrical stimulation therapies. The low power current operations include supply of power to the analog and digital portions of the low power circuitry 60. For simplicity of description, the interconnections between the cells 102 and all the components of the operational circuit 48 is not shown. In the event of a failure of one of the cells 102, the isolation circuit 110 isolates the failed cell from the other cell.

As previously discussed, the low power circuitry 60 may also include charge monitoring circuitry (e.g., control circuit 54) that is coupled to the output circuit 56 to monitor the voltage stored in the capacitors 122. The voltage stored in the capacitors 122 corresponds to the voltage that is to be delivered in the form of an electrical stimulation therapy pulse to patient 12. As is known in the art, this voltage may be in the range of 200 V to 1800 V.

To facilitate the measurements, the magnitude of the voltage to be measured may be reduced to enable the voltage to be measured by components in the charge monitoring circuit that may not be rated at the cumulative voltage present at the input. In one embodiment, a resistor voltage divider 124 is utilized for measurement of the cumulative voltage stored by the capacitors 122. The resistive voltage divider 124 is coupled in parallel with the capacitors 122 and an output of the resistive voltage divider 124 is coupled to the charge monitoring circuit. The resistive voltage divider 124 and capacitors 122 are coupled to a common node, in this case the ground node. The resistor voltage divider 124 provides a divided voltage value, the divided voltage value being a value that has a magnitude that is a fraction of the measured voltage that is stored in the capacitors 122. In other words, the divided voltage value has a magnitude that is less than the magnitude of the cumulative voltage that is stored in the capacitors 122.

The resistive voltage divider 124 is configured having a first resistor and a second resistor, the values of the first and second resistors being selected to enable the output voltage generated by the resistive voltage divider 124 to be a fraction of the cumulative voltage stored by the capacitors 122. The charge monitoring circuit issues the control signal CS that controls an on-time for delivery of charge from the first and second cells 102 based on the value of the output voltage from the resistive voltage divider 124. In particular, the control signal CS controls the duration of actuation of each of the switches 108*a*, 108*b*.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical device, comprising:
   a transformer having:
      a magnetic core;
      a plurality of primary windings wound around the core comprising at least a first primary winding and a second primary winding; and
      a plurality of secondary windings wound around the core and magnetically coupled to the primary windings;
   a power source having at least a first cell and a second cell, the first cell being coupled to the first primary winding defining a first current path between the first cell and the transformer and the second cell being coupled to the second primary winding defining a second current path between the second cell and the transformer;
   a first switching element coupled along the first current path;
   a second switching element coupled along the second current path;
   a plurality of capacitors coupled in a series configuration, wherein each of the plurality of capacitors is coupled to a single winding of the plurality of secondary windings; and
   a low power circuit coupled to the power source for controlling the delivery of charge from the power source to the plurality of capacitors through the transformer.

2. The implantable medical device of claim 1, wherein the low power circuit is configured to control simultaneous delivery of energy from each of the first and second cells to the plurality of capacitors through the transformer.

3. The implantable medical device of claim 1, wherein the low power circuit includes:
   a charge monitoring circuit, and
   a resistive voltage divider coupled in parallel with the plurality of capacitors with an output of the resistive voltage divider being coupled to the charge monitoring circuit.

4. The implantable medical device of claim 3, wherein the resistive voltage divider is configured to measure a cumulative voltage across the plurality of capacitors and to generate a divided voltage that is a fraction of the cumulative voltage, and
   wherein the charge monitoring circuit issues a control signal to control an on-time for delivery of charge from the first and second cells responsive to the divided voltage.

5. The implantable medical device of claim 3, further comprising an isolation circuit coupled between the first cell, the second cell, and the charge monitoring circuitry, wherein the isolation circuit is configured to maintain a current isolation between the first cell and the second cell responsive to a coupling of both the first and second cells to the transformer for delivery of charge.

6. The implantable medical device of claim 3, wherein the power source, the transformer and the plurality of capacitors are coupled to a common node.

7. The implantable medical device of claim 6, wherein the charge monitoring circuit measures a cumulative voltage across the plurality of capacitors measured with respect to the common node and issues a control signal for controlling actuation of the first and second switching elements.

8. The implantable medical device of claim 1, wherein the power source, the transformer and the plurality of capacitors are coupled to a common node.

9. The implantable medical device of claim 8, wherein the low power circuit measures a cumulative voltage across the plurality of capacitors measured with respect to the common node and issues a control signal for controlling the delivery of charge from the power source.

10. The implantable medical device of claim 1, further comprising a first switching element configured to selectively couple the first cell to the plurality of primary windings and a second switching element configured to selectively couple the second cell to the plurality of primary windings.

11. The implantable medical device of claim 10, wherein the low power circuit issues a control signal to simultaneously open or close the first and second switching elements to selectively couple the first and second cells to the plurality of primary windings for delivery of charge.

12. The implantable medical device of claim 10, wherein the low power circuit monitors a cumulative voltage across the plurality of capacitors and issues the control signal to simultaneously open or close the first and second switching elements.

13. The implantable medical device of claim 1, wherein the first cell is coupled to a first single winding of the plurality of primary windings and the second cell is coupled to a second single winding of the plurality of primary windings.

14. The implantable medical device of claim 1, further comprising a diode coupled between each of the windings of the plurality of secondary windings and each capacitor coupled thereto for biasing the flow of current from the transformer to each of the plurality of capacitors.

15. The implantable medical device of claim 1, wherein the first cell comprises a first cathode and the second cell comprises a second cathode, and wherein a first winding of the plurality of primary windings is directly coupled to the first cathode and a second winding of the plurality of primary windings is directly coupled to the second cathode.

16. The implantable medical device of claim 1, further comprising a charge monitoring circuit for monitoring a state of charge of each of the first and second cells.

17. The implantable medical device of claim 16, wherein the charge monitoring circuit issues a control signal for controlling a rate of average current delivery from each of the first and second cells to maintain a voltage difference between the first and second cells within a predetermined voltage value.

18. The implantable medical device of claim 16, wherein the first switching element is configured to selectively couple the first cell to the first primary winding of the plurality of primary windings and the second switching element is configured to selectively couple the second cell to the second primary winding of the plurality of primary windings, and wherein the charge monitoring circuit issues the control signal to separately open or close the first and second switching elements to selectively couple the first and second cells to the respective first and second primary windings of the plurality of primary windings for delivery of charge responsive to the voltage difference exceeding the predetermined voltage value.

19. The implantable medical device of claim 16, wherein the charge monitoring circuit monitors the state of charge through coulomb counting.

20. The implantable medical device of claim 16, wherein the charge monitoring circuit monitors the state of charge through voltage measurement.

21. The implantable medical device of claim 1, wherein each of the windings of the plurality of secondary windings are interlaced along a length of each of the secondary windings.

22. The implantable medical device of claim 1, wherein the plurality of secondary windings comprises six wires.

23. The implantable medical device of claim 1, wherein the first switching element is configured to initiate current flow from the first cell to the first primary winding upon actuation of the first switching element into a closed position, and the second switching element is configured to initiate current flow from the second cell to the second primary winding upon actuation of the second switching element into a closed position.

* * * * *